United States Patent [19]
Tadahiro

[11] Patent Number: 4,764,945
[45] Date of Patent: Aug. 16, 1988

[54] METHOD OF MEASURING LAYER THICKNESS AND COMPOSITION OF ALLOY PLATING

[75] Inventor: Abe Tadahiro, Chiba, Japan
[73] Assignee: Kawasaki Steel Corp., Hyogo, Japan
[21] Appl. No.: 860,190
[22] PCT Filed: Oct. 3, 1985
[86] PCT No.: PCT/JP85/00551
  § 371 Date: Apr. 24, 1986
  § 102(e) Date: Apr. 24, 1986
[87] PCT Pub. No.: WO86/02164
  PCT Pub. Date: Apr. 10, 1986

[30] Foreign Application Priority Data
Oct. 5, 1984 [JP] Japan ............................... 59-209097
Oct. 5, 1984 [JP] Japan ............................... 59-209098

[51] Int. Cl.[4] ................... G01B 15/02; G01N 23/223
[52] U.S. Cl. ........................................ 378/50; 378/44; 378/71
[58] Field of Search ............... 378/44, 45, 49, 50, 378/70, 71, 86, 88–90, 46

[56] References Cited
U.S. PATENT DOCUMENTS
| | | | |
|---|---|---|---|
| 2,711,480 | 6/1955 | Friedman | 378/50 |
| 3,903,414 | 9/1975 | Herbstein et al. | 378/46 |
| 3,925,678 | 12/1975 | Eberspaecher et al. | 378/44 |
| 4,169,228 | 9/1979 | Briska et al. | 378/50 |

FOREIGN PATENT DOCUMENTS
| | | | |
|---|---|---|---|
| 2636145 | 3/1977 | Fed. Rep. of Germany | 378/71 |
| 0017695 | 2/1975 | Japan. | |
| 0157145 | 9/1982 | Japan. | |
| 0150845 | 9/1983 | Japan. | |
| 0223047 | 12/1983 | Japan | 378/44 |

Primary Examiner—Craig E. Church
Assistant Examiner—John C. Freeman
Attorney, Agent, or Firm—Parkhurst & Oliff

[57] ABSTRACT

Methods of measuring the thickness or thicknesses and the composition or compositions of an alloy plating having one layer or two layers different in composition from each other, wherein the alloy plating includes a metal identical with a substrate metal, suitable for use in analyzing a Zn—Fe group one layer or two layer alloy-plated steel plate. Characteristic X-rays and white X-rays irradiate an object (112, 10, 210) to be measured. A diffraction angle ($2\theta$) of diffracted X-rays of the characteristic X-rays, which are diffracted by an intermetallic compound of the alloy plating, is measured; the composition of the alloy plating is measured from the diffraction angle, an intensity or intensities of fluorescent X-rays from an object to be measured are detected, wherein the flourescent X-rays generated by the white X-rays; and the thickness or thicknesses of the alloy plating are measured from the intensity or intensities of the fluorescent X-rays and the composition of the alloy plating.

12 Claims, 6 Drawing Sheets

METHOD OF MEASURING LAYER THICKNESS AND COMPOSITION OF ALLOY PLATING

TECHNICAL FIELD

This invention relates to a method of measuring a layer thickness and composition of an alloy plating, and more particularly to a method of measuring the layer thickness and the composition of an alloy plating including a metal identical with a substrate metal. This method is suitable for use in the analysis of a Zn—Fe group alloy-plated steel plate of one or two layers.

BACKGROUND ART

Various plated steel plates having excellent anticorrosion properties, workability, coating properties, weldability and the like have been developed for use in motor vehicle bodies, electrical household appliances and building materials, and are widely used. In order to stabilize the production quality of these plated steel plates, it is essential to analyze the thickness (deposit value) and the composition (content) of the plating to carry out the process control.

For a steel plate having a plating composed of a content other than Fe, such as a Zn plated steel plate and a Zn—Ni alloy-plated steel plate, the thickness and the composition of the plating can be comparatively easily analyzed using fluorescent X-rays, and apparatus for this type of analysis has been put to practice.

However, analysis of a Zn-Fe group alloy-plated steel plate, the outstanding characteristic feature of which has been noted recently, has been impossible by the ordinary method of fluorescent X-rays because the intesity of the Zn fluorescent X-rays is varied due to the content of Zn or Fe in the plating and the thickness of the plating. In addition, for Fe, a large quantity of Fe fluorescent X-rays are generated from a substrate steel plate, and these fluorescent X-rays cannot be discriminated from the Fe fluorescent X-rays in the plating.

For this reason, the following methods of analyzing the Zn—Fe group one layer alloy-plated steel plate have heretofore been proposed. One method is proposed in Japanese Patent Laid-Open No. 24680/1980, wherein, using a Zn plated steel plate which has been subjected to the Zn—Fe alloying process, a fluorescent X-ray intensity of a metal other than Fe, i.e. that of Zn, is measured by two measuring angles differing from each other. Using predetermined simultaneous equations on the basis of both measured values, the thickness of the plating on the plated steel plate and the degree of alloying (Fe content) are obtained. According to this method, Zn fluorescent X-ray intensities of a sufficiently thick pure Zn sample are previously measured by two measuring angles, and subsequently, a Zn fluorescent X-ray intensity of a Zn alloy-plated steel plate is measured by the same X-ray spectroscope. Analysis is made of the ratio with the pure Zn fluorescent X-ray intensity obtained previously at the respective measuring angles. The fluorescent X-ray quantitative method wherein the measuring angles are varied has been the basic theory of the method of analyzing the fluorescent X-rays published in textbooks from old times and is well known to everyone.

A second method is proposed in Japanese Patent Laid-Open No. 223047/1983, wherein an Fe content in the plating of a Zn—Fe alloy-plated steel plate is obtained from an Fe fluorescent X-ray intensity by a first excitation ray incident angle and the fluorescent X-ray measuring angle, both of which Fe fluorescent X-rays from the substrate steel plate are not substantially detected. The thickness of the plating is obtained from an Fe fluorescent X-ray intensity by a second excitation ray incident angle and a fluorescent X-ray measuring angle, both of which Fe fluorescent X-rays from the substrate steel plate can be detected.

However, since a plated steel plate flows at a speed as high as 100 meter/min, for example on a production line, the plated steel plate is bound to flutter more or less. The influence of this fluttering is received only by the steel plate, so that, according to the former method proposed in Patent Laid-Open No. 24680/1980, the analyzing accuracy is necessarily deteriorated.

In general, the thickness of the plating of the alloy-plated steel plate is as thin as 20–30 $g/m^2$ (about 3–4 micrometer). If the fluorescent X-rays are strong enough to accurately measure a metal in the plating by the latter method proposed in Patent Laid-Open No. 233047/1983, then it is impossible to excite only the thin plated layer, and the substrate metal as well as the thin plated layer are bound to be excited. In consequence, both the fluorescent X-ray intensities of Fe in the plating and Fe in the substrate steel plate are measured, so that an accurate analysis cannot be made. Further, when an on-line systemizing is intended, with a low incident angle=measuring angle=5° adopted in the first X-ray optical system, construction of such proposed apparatuses as described above have been impracticable, because of the size of an X-ray tube, construction of an X-ray spectroscopic system, a protective cover of an analysis meter and the like.

In consequence, both the methods which have been proposed are disadvantageous. Therefore, a method of chemical analysis has been relied on wherein only the plated layer is dissolved and removed by electrolysis or a suitable acid. The thickness of the plating is obtained from the value of removal, and an Fe content in the plating is obtained through chemical analysis of the value of Fe in the solution. However, it is extremely difficult to dissolve only the plated layer without dissolving the substrate steel plate. It requires a considerably high skill level and a long period of time to conduct this chemical analysis method. Moreover, this analysis is a destructive analysis to collect samples from a product and the on-line systemizing cannot be attained, thus presenting such a disadvantage that the reflection of measured results to the process control is delayed to a great extent.

It is very difficult to analyze even the Zn—Fe group of a one layer alloy-plated steel plate as described above. For a Zn—Fe group two layer alloy-plated steel plate having a first layer with a Zn—Fe alloy plating and a second layer with an Fe plating having Fe as the chief content, the problem becomes further complicated and measurement with high accuracy becomes extremely difficult.

In an invention analogous to the present invention, apparatus for continuously inspecting a quality of steel plate has been proposed in Japanese Patent Laid-Open No. 17695/1975. The apparatus thereof comprises: means for causing characteristic X-rays and white X-rays to irradiate a continuously moving steel plate at a predetermined angle; means for detecting diffracted X-rays which have wavelengths satisfying a condition of Bragg and fluorescent X-rays from this irradiating point; and means for analyzing these detection signals to sense intensity values of respective aggregate structures, elements, etc. However, this invention is different in object and constitution from the present invention, and moreover, the detection of the thickness of plating is not conducted.

The present invention has been developed to obviate the disadvantages of the prior art and has as one object the provision of a method of measuring the thickness and the composition of an alloy plating, wherein the thickness and the composition of a one layer alloy plating which includes a metal identical to a substrate metal can be measured simultaneously and non-destructively.

The present invention has as another object the provision of a method of measuring the thickness and the composition of an alloy plating, wherein the thickness and the composition of an alloy plating having two layers different in composition from each other and which include a metal identical to a substrate metal, can be measured simultaneously and non-destructively.

DISCLOSURE OF THE INVENTION

According to the present invention, a fluorescent X-ray analyzing method and an X-ray diffracting method are simultaneously used to measure the thickness and the composition of a one layer alloy plating which includes a metal identical with a substrate metal. As shown in FIG. 1, the characteristic X-rays and the white X-rays irradiate an object to be measured; a diffraction angle of diffracted X-rays of the characteristic X-rays, which are diffracted by an intermetallic compound of the alloy plating, is detected; the composition of the alloy plating is measured from the diffraction angle; an intensity of fluorescent X-rays from a metal different from the substrate metal in the alloy plating, which fluorescent X-rays are generated by the white X-rays, is detected; and the thickness of the alloy plating is simultaneously measured from the intensity of the fluorescent X-rays and the composition of the alloy plating. With this process, the thickness and the composition of the one layer alloy plating can be measured simultaneously and non-destructively.

Furthermore, according to the present invention, the thickness and the composition of an alloy plating having two layers different in composition from each other and including a metal identical with a substrate metal can be measured. As shown in FIG. 2, characteristic X-rays and white X-rays irradiate an object to be measured; a diffraction angle of diffracted X-rays of the characteristic X-rays, which are diffracted by an intermetallic compound of a first layer (bottom layer) of the alloy plating, is detected; the composition of the first layer of the alloy plating is measured from the diffraction angle; intensities of fluorescent X-rays from a substrate metal, a metal identical with the substrate metal in the alloy plating and a metal different from the substrate metal in the alloy plating, which fluorescent X-rays are generated by the white X-rays, are respectively detected by two measuring angles; and the thickness of plating of the first layer and a second layer (top layer) are simultaneously measured from the intensities of the fluorescent X-rays and the composition of the first layer of the alloy plating. With this process, in one cycle of measuring, the thickness and the compositions of the alloy plating having two layers of different composition and including a metal identical with the substrate metal are simultaneously measured.

Further, a specific form of the present invention is an arrangement wherein the characteristic X-rays and the white X-rays are generated from a single X-ray source, for example an X-ray tube of Cr target, so that the measuring apparatus can be simplified in construction.

Another specific form of the present invention is an arrangement wherein the characteristic X-rays are generated from an X-ray tube of Cr and the white X-rays are generated from an X-ray tube of W target, so that strong white X-rays can be generated.

A further specific form of the present invention is an arrangment wherein the incident angles of the X-rays are minimized in values, so that the intrusion of the X-rays into the substrate metal becomes shallow, thereby increasing information from the alloy plating.

A detailed description of the method of the present invention will be given by way of example of an Zn—Fe group two layer alloy-plated steel plate, which has a first layer of a Zn—Fe alloy plating and a second layer of a Fe plating having Fe as the chief constituent.

In analyzing the above-described two layer alloy-plated steel plate, initially a well known method of varying the measuring angles is considered. This method is disadvantageous in that, as described above, with the Zn—Fe alloy-plated steel plate, only the intensities of Zn fluorescent X-rays are compared with pure Zn. To obviate this disadvantage, a study has been made of a method of using Fe fluorescent X-rays. This is because the fluttering of the alloy-plated steel plate on the production line affects the Fe fluorescent X-rays as well as the Zn fluorescent X-rays, whereby, when the analysis is made by use of both X-rays, the adverse influence can be eliminated.

Now, as shown in FIG. 3, when X-rays are caused to fall into the Zn—Fe group two layer alloy-plated steel plate 10 at an incident angle of $\psi$, the whole intensities of fluorescent X-rays of an element to be measured, which is measured by a measuring angle $\psi_1$, can be theoretically represented by the following equation:

$$X = X_1 + X_2 + X_3 \tag{1}$$

where $X_1$ is an intensity of fluorescent X-rays of an element to be measured from the second layer (top layer), $X_2$ is an intensity of fluorescent X-rays of an element to be measured from the first layer (bottom layer), and $X_3$ is an intensity of fluorescent X-rays of an element to be measured from the substrate steel plate.

$X_1$, $X_2$ and $X_3$ are represented by the following equations when the thickness of the second layer (plating deposit value) is $T_1$, the thickness of the first layer (plating deposit value) is $T_2$, the content of the element to be measured in the second layer is $W_1$, the content of the element to be measured in the first layer is $W_2$ and the content of the element to be measured in the substrate steel plate is $W_3$:

$$X_1 = (ki/\sin\psi) \times I_0 \times [1 - \exp\{-(\mu_1^P/\sin\psi + \mu_1^S/\sin\psi_1) \times T_1\}] \times [\{W_1 \times (\mu/p)^i\} \div (\mu_1^P/\sin\psi + \mu_1^S/\sin\psi_1)] \tag{2}$$

-continued $$X_2 = (k_i/\sin\psi) \times I_0 \times \exp\{-(\mu_1^P/\sin\psi + \mu_1^S/\sin\psi_1) \times T_1\} \times [1 - \exp\{-(\mu_2^P/\sin\psi + \mu_2^S/\sin\psi_1) \times T_2\}] \times [\{W_2 \times (\mu/p)'\} \div (\mu_2^P/\sin\psi + \mu_2^S/\sin\psi_1)] \quad (3)$$

$$X_3 = (k_i/\sin\psi) \times I_0 \times \exp\{-(\mu_1^P/\sin\psi + \mu_1^S/\sin\psi_1) \times T_1\} \times \exp\{-(\mu_2^P/\sin\psi + \mu_2^S/\sin\psi_i) \times T_2\} \times [\{W_3 \times (\mu/p)'\} \div (\mu_3^P/\sin\psi + \mu_3^S/\sin\psi_1)] \quad (4)$$

where $k_i$ is a constant, and $\mu_i^P$ and $\mu_i^S$ (i=1-3) are mass absorption coefficients of the respective layers to the incident rays (P) and the measured rays (S) respectively.

When a mass absorption coefficient of the element to be measured is $(\mu/p)$ and a mass absorption coefficient of the coexistent element is $(\mu/p)'$, $\mu_i^P$ and $\mu_i^S$ are represented by the following equations:

$$\mu_i^P = W_i X(\mu/p)^P + (100 - W_i) X(\mu/p)^{P'} \quad (5)$$

$$\mu_i^S = W_i X(\mu/p)^S + (100 - W_i) X(\mu/p)^{S'} \quad (6)$$

Since the incident angle $\psi$ is made constant for practical use, the terms of the coefficient (ki/sin $\psi$) of the right members of the above-mentioned equations (1)-(3) become constant, too.

In consequence, as shown in FIG. 4, the white X-rays generated from an X-ray tube 12 irradiate a Zn—Fe group two layer alloy-plated steel plate 10 at an incident angle, and, if the intensity of fluorescent X-rays generated is simultaneously measured by detectors 18₁ and 18₂ for Zn fluorescent X-rays and detectors 20₁ and 20₂ for Fe fluorescent X-rays through spectroscopic crystals 14₁ and 14₂ for Zn fluorescent X-rays and spectroscopic crystals 16₁ and 16₂ for Fe fluorescent X-rays, which are provided in two measuring angles $\psi_1$ and $\psi_2$, then, simultaneous equations on Zn are established by the two measuring angles $\psi_1$ and $\psi_2$ and also simultaneous equations on Fe are established by the two measuring angles $\psi_1$ and $\psi_2$. Therefore, a converging thickness Ti and a content Wi of an element to be measured, the errors of which are minimized, are obtained from the two types of simultaneous equations. However, only two unknown terms can be solved from the above information. In consequence, according to the above-described method, the analysis can be made only on one layer after another. Then, firstly, after the plating of the first layer, the intensity of the fluorescent X-rays is measured, the thickness T₂ and the content W₂ of the element to be measured of the first layer plating are obtained from the combination of the aforesaid theoretical equations. Subsequently, after the plating of the second layer, the intensity of the fluorescent X-rays is also measured, and analyzed values of the thickness T₂ and the content W₂ of the first layer are inserted to obtain the thickness T₁ and the content W₁ of the element to be measured of the second layer plating. However, according to the above-described method, in the case of on-line systemizing, two analysis devices are required. Moreover, after the plating of the first layer, the measurement is conducted in the wet state, whereby the intensities of fluorescent X-rays of Zn and Fe are varied due to a difference in absorption value of the incident X-rays and the fluorescent X-rays by the value of moisture on the plated steel plate, a variation in scattering value of Compton electrons and so on, so that accurate analysis is difficult to make. Naturally, lowered analyzed values of the first layer lead to deteriorated analyzed values of the second layer.

In general, in the case of the Zn—Fe group two layer alloy-plated steel plate which has a first layer of a Zn—Fe alloy plating and a second layer of a Fe plating having Fe as the chief constituent, the analysis is needed for three values, i.e. the thickness T₂ and the composition (content) W₂ of the first layer and the thickness T₁ of the second layer. In consequence, when one of these is analyzed by some method, other values can be obtained by solving the above-mentioned simultaneous equations.

Then, the inventor of this invention has thought of simultaneously using the X-ray diffraction method. More specifically, in respective phases formed by the Zn—Fe intermetallic compound, the X-ray diffraction angle $2\theta$ is varied proportionally to the content of Fe (or Zn) respectively. FIG. 5 shows an example of the variation. In consequence, if the relationship between the X-ray diffraction angle $2\theta$ and the Fe content (%) is as shown in FIG. 5 on an arbitrary lattice plane of a phase (crystal) formed in the Zn—Fe alloy-plated layer (the first layer), then the Fe content (%) in the first layer (or Zn content (%) = 100 − Fe content (%) can be obtained by measuring the X-ray diffraction angle $2\theta$ from the alloy-plating layer.

At this time, even if the thickness T₁ of the second layer is varied, only the intensity of the diffracted X-ray is changed, and the diffraction angle $2\theta$ is not changed. Furthermore, if the second layer is formed of a Fe—Zn alloy plating different in composition from the first layer, this fact leads to a difference in the X-ray diffraction angle $2\theta$ due to the difference in crystalline structure. In consequence, from the X-ray diffraction angles $2\theta$ of the both layers, the respective compositions (Fe content) of the first and the second layers can be analyzed.

The present invention has been invented on the basis of the knowledge described above.

BRIEF DDESCRIPTION OF THE DRAWINGS

Figure 8:
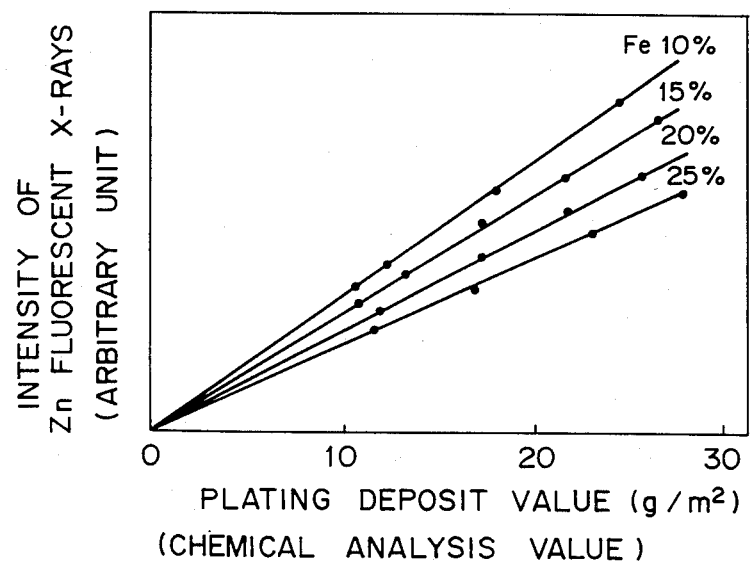
Figure 9:
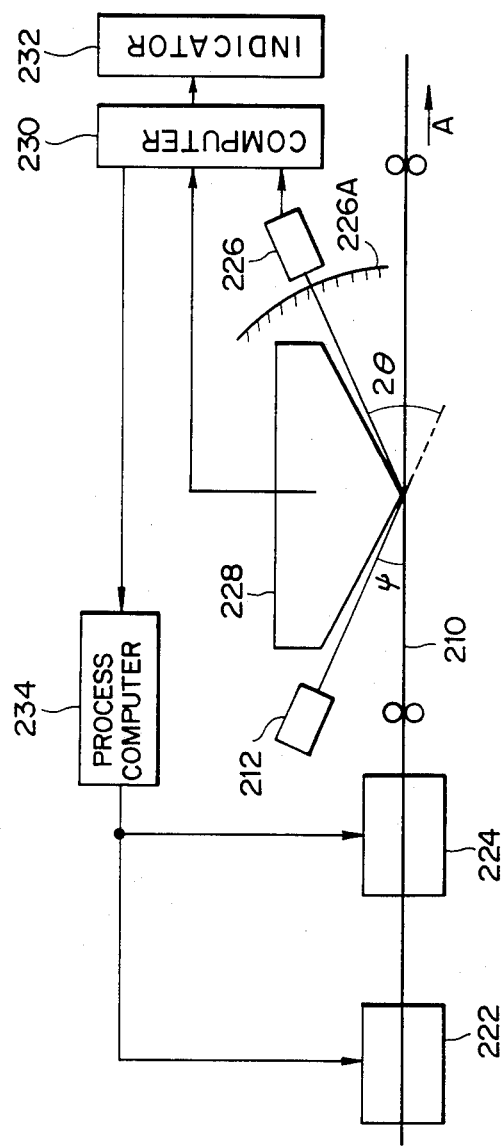

FIG. 8 is a chart showing an example of the relationship between the Zn fluorescent X-ray intensity, the Fe content and the plating deposit value (thickness of plating), for explaining the principle of the present invention; and FIG. 9 is a block diagram showing the arrangement of an embodiment of the apparatus for measuring the thickness and the composition of the alloy plating of the Zn—Fe group two layer alloy-plated steel plate, which is a second embodiment of the present invention.

BEST MODE FOR CARRYING OUT THE INVENTION

Detailed description will hereunder be given of the embodiments of the present invention with reference to the drawings.

Figure 6:
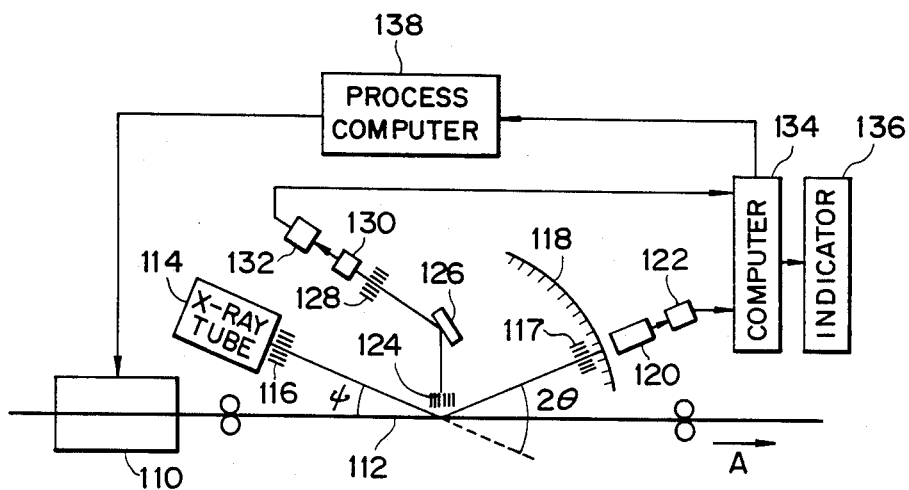
FIG. 6 is a block diagram showing the arrangement of an embodiment of the apparatus for measuring the thickness and the composition of the alloy plating of the Zn—Fe one layer alloy-plated steel plate, which is a first embodiment of the present invention.

In the first embodiment of the present invention, the present invention is applied to the measurement of the thickness and the composition of the alloy plating of a Zn—Fe one layer alloy-plated steel plate. The embodiment of the measuring apparatus is constructed as shown in FIG. 6.

In this first embodiment, a Zn—Fe one layer alloy-plated steel plate 112 which has been plated in a plating bath 110 is being conveyed in a direction indicated by an arrow A. A powerful X-ray tube 114 for generating characteristic X-rays having a suitable wavelength, such as Cr target, is provided at a proper position on a horizontal conveying section (or a vertical conveying section) for the Zn—Fe one layer alloy-plated steel plate 112. X-rays emitted from the X-ray tube 114 are made to fall onto the Zn—Fe one layer alloy-plated steel plate 112 at an incident angle through a solar slit 116. Then, the X-rays are diffracted through the following formula of Bragg by respective crystal lattice planes of the phases of the Zn—Fe intermetallic compound formed in the alloy plating layer of the Zn—Fe alloy-plated steel plate 112:

$$\lambda = 2d \sin \theta \qquad (7)$$

where $\lambda$ is a wavelength, $\theta$ is an angle, and d is the distance between the crystal lattice planes of the Zn—Fe intermetallic compound.

At this time, in the crystal of the Zn—Fe intermetallic compound, the lattice constant varies due to the content of Fe (or Zn), whereby the X-ray diffraction angle $2\theta$ is deviated. More specifically, since the X-ray diffraction angle $2\theta$ is varied due to the content of the Fe (or Zn), the relationship between the content (%) of Fe (or Zn) and the X-ray diffraction angle $2\theta$ is obtained on an arbitrary crystal lattice plane, as shown in an example in FIG. 5, by a solar slit 117, a goniometer 118, a diffracted X-ray detector 120 and a counter circuit 122. When the X-ray diffraction angle $2\theta$ is measured by the same crystal lattice plane from the layer of the alloy plating, the Fe content (%) in the alloy plating (or the Zn content (%) = 100 − Fe content (%)) in the alloy plating of the Zn—Fe one layer alloy-plated steel plate 112 can be obtained.

Figure 7:
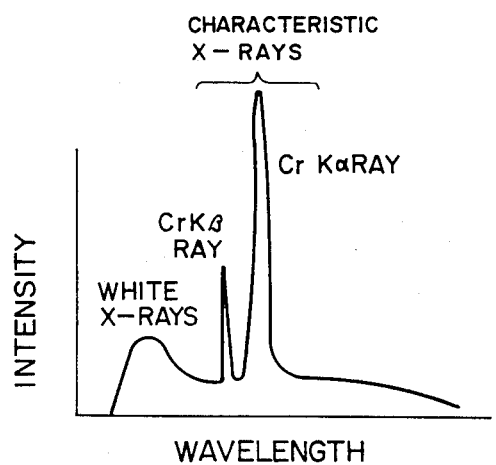
FIG. 7 is a chart showing the wavelength distribution of the X-rays generated from the Cr target X-ray tube as used in this embodiment.

On the other hand, since the X-ray tube 114 generating the characteristic X-ray normally generates the white X-rays as well, as shown in FIG. 7, the white X-rays are effectively utilized in this first embodiment. More specifically, the white X-rays excite a metal contained in the Zn—Fe one layer alloy-plated steel plate 112, and generate the fluorescent X-rays having a wavelength commensurate to the metal, so that the analysis is then made by use of the Zn fluorescent X-rays. More specifically, from the fluorescent X-rays of the metal contained in Zn—Fe one layer alloy-plated steel plate 112, which metal is excited by the white X-rays, only the Zn fluorescent X-rays are spectroscopically divided by a spectroscopic crystal 126 through a solar slit 124, and the intensity of the Zn fluorescent X-rays is measured by a fluorescent X-ray detector 130 and a counter circuit 132 through a solar slit 128.

Since the intensity of the Zn fluorescent X-rays, which is detected by this fluorescent X-ray detector 130, is varied due to the Zn (or Fe) content and the thickness of the Zn—Fe one layer alloy plating as described above, the analysis cannot be made by a normal method. However, as described above, the Zn content in the alloy plating can be analyzed by the X-ray diffraction method, so that the thickness of plating can be obtained from the Zn fluorescent X-ray intensity.

FIG. 8 shows an example of a study of the relationship between the Zn fluorescent X-ray intensity and the thickness of plating (plating deposit value). It is apparent that, if the Fe content (%) is found, then the thickness of plating can be easily known from the Zn fluorescent X-ray intensity. At this time, the thickness of plating may be obtained in such a manner that an influence quantity of Fe to the Zn fluorescent X-ray intensity is previously obtained and is corrected by the Fe content.

Additionally, it would be effective if the incident angle $\psi$ of the X-rays would be minimized in consideration of the influence of fluttering and the X-ray diffraction angle $2\theta$ of the measuring lattice plane, because the intrusion of the X-rays into the substrate steel plate becomes shallow, and consequently, information from the alloyed plating is increased.

A series of X-rays diffraction intensities obtained by scanning to detect the diffraction angle $2\theta$ of an arbitrary crystal lattice plane according to the above-described X-ray diffraction method and the aforesaid fluorescent X-ray intensity are simultaneously measured and inputted to a computer 134, respectively. In this computer 134, various calculations are performed and the Fe content and the thickness of plating in the alloy plating are obtained. The results are displayed in an indicator 136 on the line of the spot and inputted to a process computer 138 simultaneously, whereby plating conditions of the plating bath 110 and the like are controlled on the basis of the analyzed values.

In this first embodiment, both the characteristic X-rays and the white X-rays are generated from the single X-ray tube 114, so that the measuring apparatus is simplified in construction. Additionally, the method of generating the characteristic X-rays and the white X-rays need not necessarily be limited to this, and two X-ray tubes including an X-ray tube of Cr target, for example, for generating the characteristic X-rays, and an X-ray tube of W target, for example, for generating white X-rays high in intensity, may be used or other X-ray sources may be utilized.

In the first embodiment, the present invention has been applied to the measurement of the thickness and the composition of alloy plating of the Zn—Fe one layer alloy-plated steel plate; however, the scope of application of the present invention need not necessarily be limited to this, and it is apparent that the present invention may be applied to all of the measurements of the thickness and the composition of one layer alloy plating including a metal identical with the substrate metal.

Detailed description will hereunder be given of one embodiment of the apparatus for measuring the thickness and the composition of plating of the Zn—Fe group two layer alloy-plated steel plate, which is the second embodiment of the present invention.

This second embodiment is constructed as shown in FIG. 9, wherein a Zn—Fe two layer alloy-plated steel plate 210, which has a Zn—Fe alloy plating applied thereto in a first plating bath 222 and a Fe plating having Fe as a main constituent applied thereto in a second plating bath 224, is being conveyed in a direction indicated by an arrow A. A powerful X-ray tube 212 for generating characteristic X-rays having a suitable wavelength, such as Cr target, is provided at a proper position on a horizontal conveying section (or a vertical conveying section) for the Zn—Fe group two layer alloy-plated steel plate 210, and X-rays emitted from the X-ray tube 212 are made to fall onto the Zn—Fe group two layer alloy-plated steel plate 20 at an incident angle $\psi$. Then, the X-rays are diffracted through the formula of Bragg shown in (7) above described by respective lattice planes of the phases (crystal) of the Zn—Fe intermetallic compound formed in the first layer of the Zn—Fe group two layer alloy-plated steel plate 210.

Figure 5:
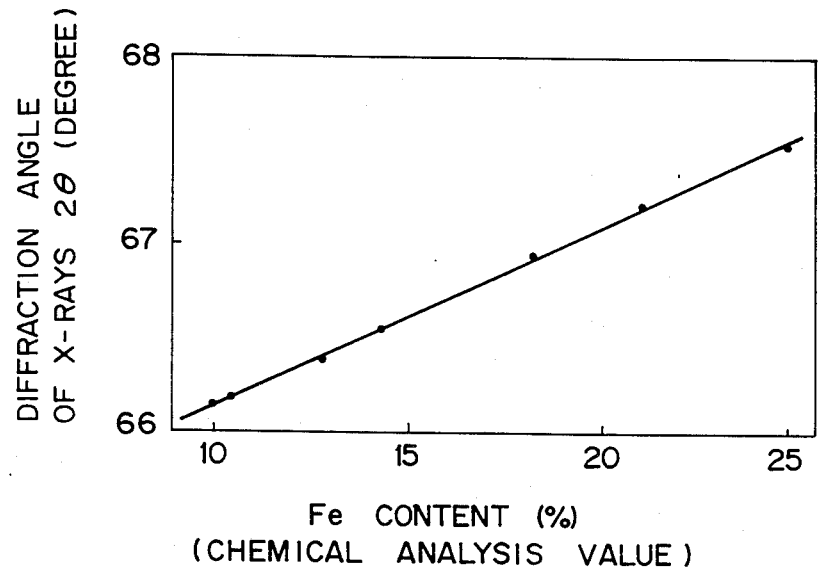
FIG. 5 is a chart showing an example of the relationship between the X-ray diffraction angle and the Fe content for explaining the principle of the present invention.

In consequence, when the X-ray diffraction angle $2\theta$ is measured by an X-ray diffraction device 226 including a goniometer 226A, the composition of the first layer, i.e. the Zn—Fe alloy-plated layer, can be analyzed from the relationship shown in FIG. 5.

Figure 1:
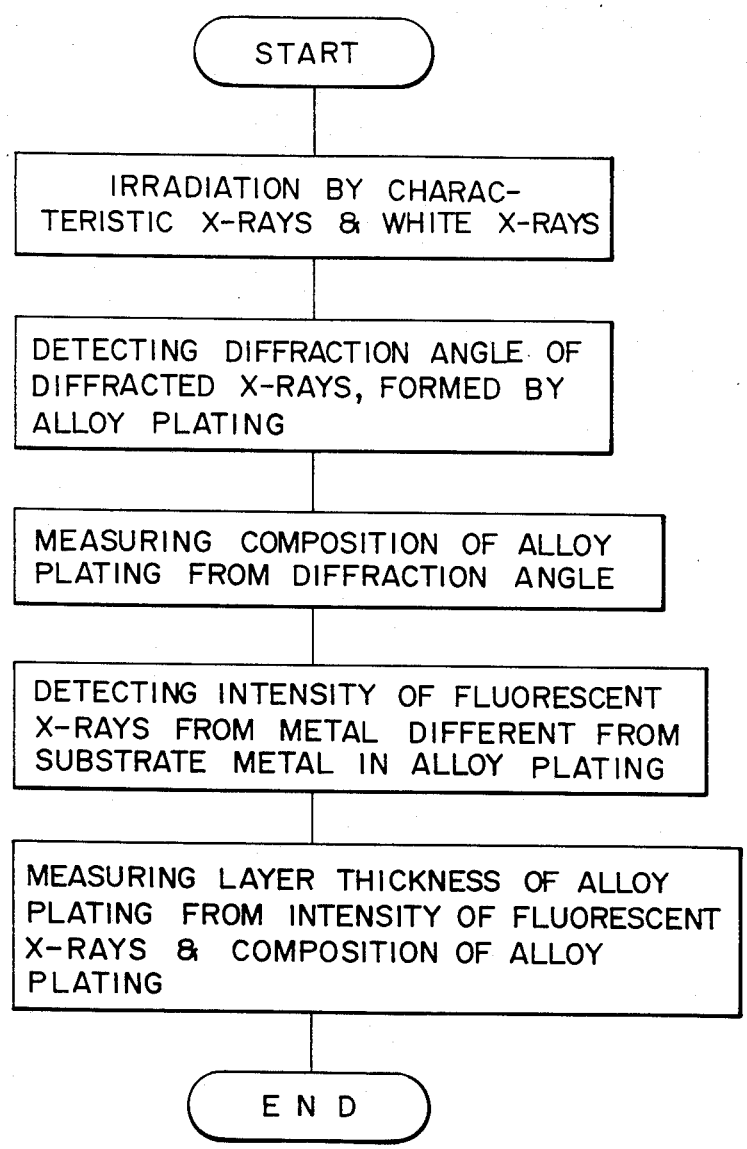
FIG. 1 is a flow chart outlining the method of measuring the thickness and the composition of the one layer alloy plating according to the present invention.
Figure 2:
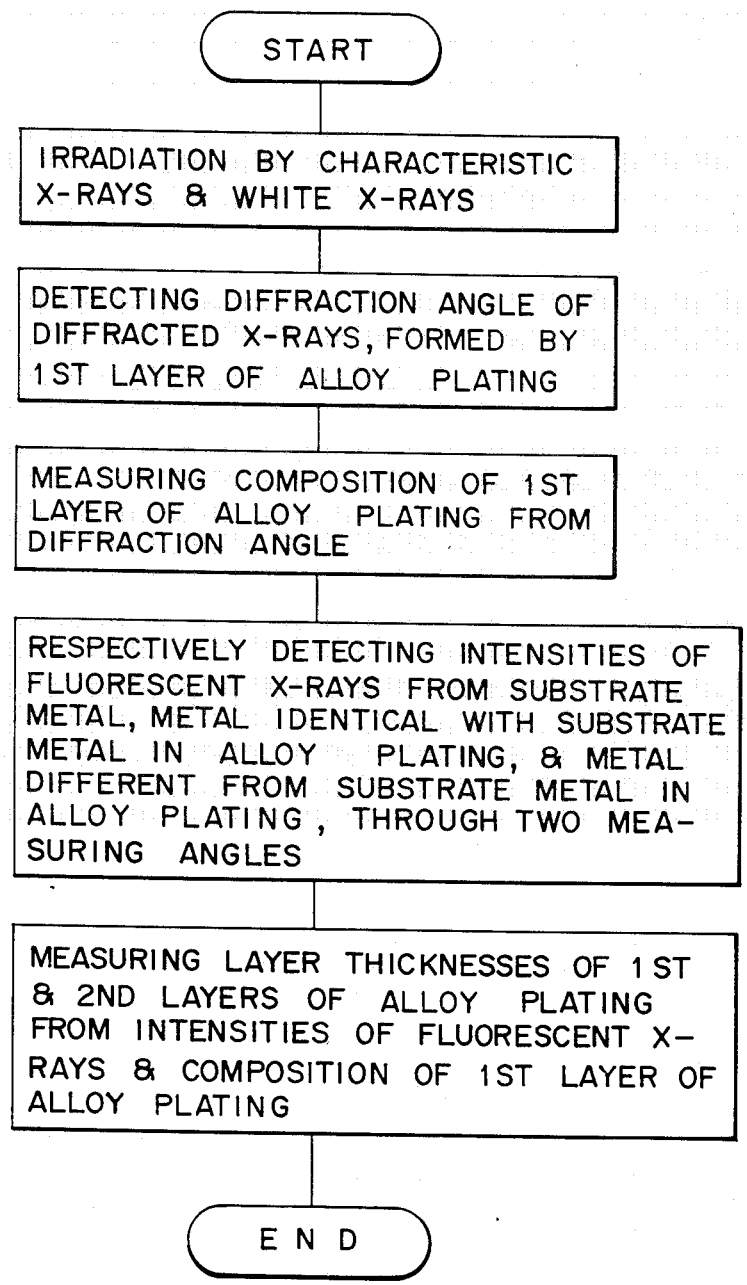
FIG. 2 is a flow chart outlining the method of measuring the thicknesses and the compositions of the two layer alloy plating according to the invention.
Figure 3:
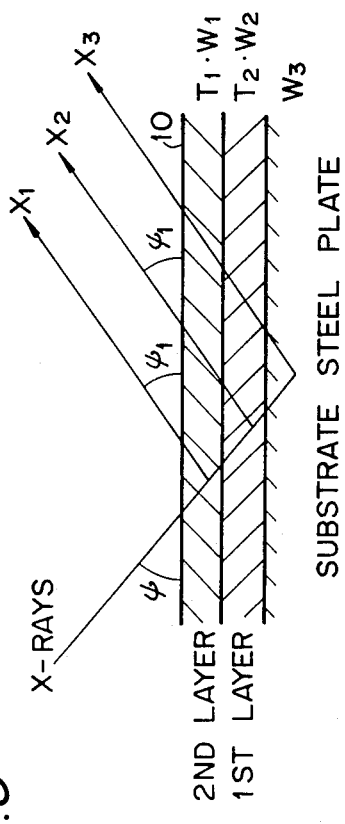
FIG. 3 is a sectional view showing the state of incidence of the X-rays to the two layer alloy-plated steel plate and the conditions of the generation of the fluorescent X-rays for explaining the principle of the present invention.
Figure 4:
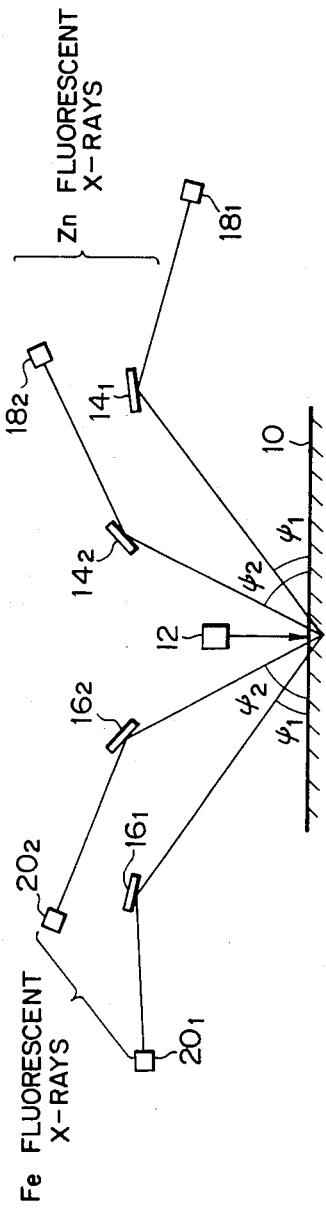
FIG. 4 is a sectional view showing the theoretical construction of the apparatus for measuring the intensity of the fluorescent X-rays for explaining the principle of the present invention.

On the other hand, the white X-rays are also generated from the X-ray tube 212 as shown in FIG. 7, whereby, the white X-rays excite Zn and Fe in the Zn—Fe group two layer alloy-plated steel plate 210 to generate fluorescent X-rays. The intensity of the generated fluorescent X-rays is simultaneously measured by use of spectroscopes having two measuring angles $\psi_1$ and $\psi_2$, which are different from each other for both Zn and Fe, in a fluorescent X-ray analysis device 228 having the basic construction as shown in FIG. 4.

Also in this second embodiment, it would be effective if the incident angle $\psi$ of the X-rays would be minimized in consideration of the influence of the fluttering and the X-ray diffraction angle $2\theta$ of the measuring lattice plane, because the intrusion of the X-rays into the substrate steel plate becomes shallow, and consequently, information from the alloy plating is increased.

Values measured by the X-ray diffraction device 226 and the fluorescent X-ray analysis device 228 are inputted to a computer 230, where the composition of the first layer is analyzed firstly, the above-described simultaneous equations are solved by use of the analyzed values, and the thicknesses $T_1$ and $T_2$ of the first and the second layers are obtained. The results are displayed in an indicator 232 on the line of the spot and inputted to a process computer 234 simultaneously, and plating conditions of the plating baths 222 and 224 and the like are controlled on the basis of the analyzed values.

In this second embodiment also, the characteristic X-rays and the white X-rays are generated from the single X-ray tube 212, so that the measuring apparatus is simplified in construction. Additionally, the method of generating the characteristic X-rays and the white X-rays need not necessarily be limited to this, and two X-ray tubes including an X-ray tube of Cr target, for example, for generating the characteristic X-rays, and an X-ray tube of W target, for example, for generating white X-rays high in intensity, may be used or other X-ray sources may be utilized.

In the second embodiment as described above, the present invention has been applied to the measurement of the thickness and the compositions of alloy plating of the Zn—Fe group two layer alloy-plated steel plate; however, the scope of application of the present invention need not necessarily be limited to this, and it is apparent that the present invention may be applied to the measurement of all of the thicknesses and the compositions of plating having two layers different in composition from each other and including a metal identical with the substrate metal.

INDUSTRIAL APPLICABILITY

As has been described hereinabove, according to the present invention, it becomes possible to simultaneously and non-destructively measure the thickness and the composition of the one layer alloy plating including a metal identical with the substrate metal, of the Zn—Fe alloy-plated steel metal or the like, which has heretofore been very difficult to measure. In consequence, it becomes possible to measure on-line the thickness and the composition of the one layer alloy plating and immediately feed back analyzed results to the line, thus providing an outstanding contribution to the stable operation and improved quality of the Zn—Fe one layer alloy-plated steel plate and the like.

Furthermore, according to the present invention, it becomes possible to simultaneously and non-destructively measure the thicknesses and the compositions of respective layers of the alloy plating having two layers different in composition from each other and including a metal identical with the substrate metal, of the Zn—Fe group two layer alloy-plated steel plate, which has heretofore been very difficult to measure. In consequence, it becomes possible to conduct the analysis of the thicknesses and the compositions of the respective layers by a single apparatus and achieve the on-line systemizing. Hence, the analyzed results can be immediately fed back to the line and an outstanding contribution can be made to the stable operation and improved quality of the Zn—Fe group two layer alloy-plated steel plate and the like.

I claim:

1. A method of measuring the thickness and the composition of a one layer alloy plating including a metal identical with a substrate metal, said method comprising the steps of:

irradiating an object to be measured with characteristic X-rays and white X-rays;

detecting a diffraction angle of diffracted X-rays of said characteristic X-rays which are diffracted by an intermetallic compound of said alloy plating;

measuring the amount of the composition of said alloy plating from said diffraction angle;

detecting an intensity of fluorescent X-rays from a metal different from said substrate metal in said alloy plating, the fluorescent X-rays being generated by the white X-rays; and measuring the thickness of said alloy plating from the intensity of the fluorescent X-rays and the amount of the composition of said alloy plating.

2. A method of measuring the thickness and the composition of alloy plating as set forth in claim 1, wherein said one layer alloy plating is a Zn—Fe one layer alloy plating applied onto a steel plate.

3. A method of measuring the thickness and the composition of alloy plating as set forth in claim 1, wherein said characteristic X-rays and said white X-rays are generated from a single X-ray source.

4. A method of measuring the thickness and the composition of alloy plating as set forth in claim 3, wherein said single X-ray source is an X-ray tube with a Cr target.

5. A method of measuring the thickness and the composition of alloy plating as set forth in claim 1, wherein said characteristic X-rays are generated from an X-ray tube with a Cr target and said white X-rays are generated from an X-ray tube with a W target.

6. A method of measuring the thickness and the composition of alloy plating as set forth in claim 1, wherein an incident angle of said characteristic and said white X-rays is minimized.

7. A method of measuring the thickness and the composition of an alloy plating having two layers different in composition from each other and including a metal identical with a substrate metal, said method comprising the steps of:

irradiating an object to be measured with characteristic X-rays and white X-rays;

detecting a diffraction angle of diffracted X-rays of the characteristic X-rays which are diffracted by an intermetallic compound of a first layer of the alloy plating, said first layer being adjacent to the substrate of said object;

measuring the amount of the composition of said first layer of the alloy plating from said diffraction angle;

detecting intensities of fluorescent X-rays from a substrate metal, a metal identical with said substrate metal in the alloy plating and a metal different from said substrate metal in the alloy plating, said fluorescent X-rays being generated by said white X-rays, and said intensities being detected by two measuring angles; and measuring the thickness of said first layer and a second layer of the alloy plating from said intensities of said fluorescent X-rays and the amount of the composition of said first layer of the alloy plating.

8. A method of measuring the thickness and the composition of alloy plating as set forth in claim 7, wherein said two layers of alloy plating include a first layer of Zn—Fe alloy plating and a second layer of Fe plating having Fe as the chief content applied onto a steel plate.

9. A method of measuring the thickness and the composition of alloy plating as set forth in claim 7, wherein said characteristic X-rays and said white X-rays are generated from a single X-ray source.

10. A method of measuring the thickness and the composition of alloy plating as set forth in claim 9, wherein said single X-ray source is an X-ray tube with a Cr target.

11. A method of measuring the thickness and the composition of alloy plating as set forth in claim 7, wherein said characteristic X-rays are generated from an X-ray tube with a Cr target, and said white X-rays are generated from an X-ray tube with a W target.

12. A method of measuring the thickness and the composition of alloy plating as set forth in claim 7, wherein an incident angle of said characteristic and said white X-rays is minimized.

* * * * *

UNITED STATES PATENT AND TRADEMARK OFFICE
CERTIFICATE OF CORRECTION

PATENT NO. : 4,764,945
DATED : August 16, 1988
INVENTOR(S) : Tadahiro ABE

It is certified that error appears in the above-identified patent and that said Letters Patent is hereby corrected as shown below:

On the title page,
In Section [75] Inventor, change "Abe Tadahiro" to --Tadahiro Abe--.

Signed and Sealed this

Third Day of January, 1989

*Attest:*

DONALD J. QUIGG

*Attesting Officer*   *Commissioner of Patents and Trademarks*